United States Patent
Mammadov

(10) Patent No.: US 9,314,780 B2
(45) Date of Patent: Apr. 19, 2016

(54) PROCESS FOR PRODUCING LIGHT OLEFINS BY USING A ZSM-5-BASED CATALYST

(75) Inventor: Aghaddin Kh. Mammadov, Houston, TX (US)

(73) Assignee: SAUDI BASIC INDUSTRIES CORPORATION, Riyadh (SA)

(*) Notice: Subject to any disclaimer, the term of this patent is extended or adjusted under 35 U.S.C. 154(b) by 113 days.

(21) Appl. No.: 13/882,946

(22) PCT Filed: Oct. 25, 2011

(86) PCT No.: PCT/EP2011/005375
§ 371 (c)(1),
(2), (4) Date: May 1, 2013

(87) PCT Pub. No.: WO2012/059191
PCT Pub. Date: May 10, 2012

(65) Prior Publication Data
US 2013/0217939 A1    Aug. 22, 2013

(30) Foreign Application Priority Data
Nov. 2, 2010    (EP) .................................... 10014193

(51) Int. Cl.
*C07C 1/22*    (2006.01)
*B01J 29/48*    (2006.01)
(Continued)

(52) U.S. Cl.
CPC *B01J 29/48* (2013.01); *B01J 23/83* (2013.01); *B01J 29/40* (2013.01); *B01J 29/405* (2013.01);
(Continued)

(58) Field of Classification Search
USPC .......................................... 585/638, 639, 640
See application file for complete search history.

(56) References Cited

U.S. PATENT DOCUMENTS 3,894,106 A    7/1975    Chang et al.
3,911,041 A    10/1975   Kaeding et al.
(Continued)

FOREIGN PATENT DOCUMENTS

CN    101568508 A    10/2009
EP    0568913 A2     4/1993
(Continued)

OTHER PUBLICATIONS

Extended European Search Report for Application No. 10014193.6; Date of Mailing: Apr. 11, 2011; 8 pages.
(Continued)

*Primary Examiner* — In Suk Bullock
*Assistant Examiner* — Sharon Pregler
(74) *Attorney, Agent, or Firm* — Cantor Colburn LLP

(57) ABSTRACT

The present invention relates to a catalyst composition useful in a process for producing lower olefins from a oxygenate feedstream, a process for producing said catalyst composition and a process for producing lower olefins comprising contacting a oxygenate feedstream with the catalyst composition $M_1$-$M_2$-P/ZSM-5 with an oxygenate-comprising feedstream, wherein $M_1$ is one or more basic species, $M_2$ is one or more redox elements selected from Groups 6-8 of the Periodic Table of Elements and Sn and P is phosphorus, wherein said basic species is a molecular entity forming a weak Lewis base and/or a weak Brnsted base in the catalyst composition. In addition thereto, the present invention relates to an integrated process for producing lower olefins from a feedstream comprising hydrocarbons.

15 Claims, 2 Drawing Sheets

Figure 1:
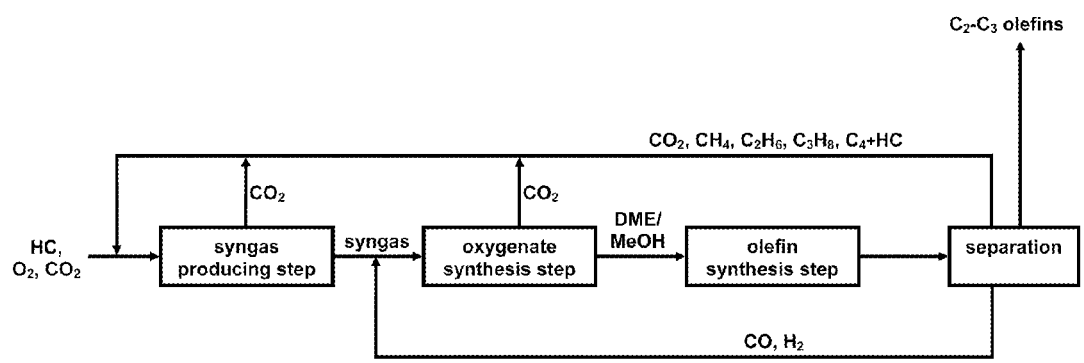

(51) Int. Cl.
*B01J 23/83* (2006.01)
*B01J 29/40* (2006.01)
*B01J 29/46* (2006.01)
*B01J 37/02* (2006.01)
*C01B 3/38* (2006.01)
*C07C 1/20* (2006.01)

(52) U.S. Cl.
CPC .............. *B01J 29/46* (2013.01); *B01J 37/0207* (2013.01); *C01B 3/38* (2013.01); *C07C 1/20* (2013.01); *C07C 1/22* (2013.01); *B01J 2229/37* (2013.01); *B01J 2229/40* (2013.01); *B01J 2229/42* (2013.01); *C01B 2203/025* (2013.01); *C01B 2203/0238* (2013.01); *C01B 2203/0244* (2013.01); *C01B 2203/062* (2013.01); *C01B 2203/1047* (2013.01); *C01B 2203/1058* (2013.01); *C01B 2203/1082* (2013.01); *C01B 2203/148* (2013.01); *C07C 2521/08* (2013.01); *C07C 2529/40* (2013.01); *C07C 2529/46* (2013.01); *C07C 2529/48* (2013.01); *Y02P 20/52* (2015.11); *Y02P 30/42* (2015.11)

(56) References Cited

U.S. PATENT DOCUMENTS

| | | | |
|---|---|---|---|
| 4,025,575 | A | 5/1977 | Chang et al. |
| 4,025,576 | A | 5/1977 | Chang et al. |
| 4,049,573 | A | 9/1977 | Kaeding |
| 4,052,479 | A | 10/1977 | Chang et al. |
| 4,062,905 | A | 12/1977 | Chang et al. |
| 4,440,871 | A | 4/1984 | Lok et al. |
| 4,849,575 | A | 7/1989 | Lewis |
| 5,367,100 | A | 11/1994 | Gongwei et al. |
| 7,132,580 | B1 | 11/2006 | Senetar |
| 2006/0216227 | A1 | 9/2006 | Idem et al. |
| 2007/0049647 | A1 | 3/2007 | Van Egmond et al. |
| 2007/0259972 | A1* | 11/2007 | Lattner et al. ............... 518/700 |
| 2008/0033225 | A1 | 2/2008 | Hall et al. |
| 2008/0103345 | A1 | 5/2008 | Levin et al. |
| 2008/0224097 | A1 | 9/2008 | Fujie et al. |
| 2008/0242908 | A1 | 10/2008 | McGlamery et al. |
| 2008/0260628 | A1 | 10/2008 | Moon et al. |
| 2009/0292148 | A1 | 11/2009 | Gracey et al. |
| 2011/0071264 | A1* | 3/2011 | Nesterenko et al. ............ 526/76 |

FOREIGN PATENT DOCUMENTS

| | | |
|---|---|---|
| EP | 1685897 A2 | 8/2006 |
| EP | 1762299 A1 | 3/2007 |
| EP | 2143700 A1 | 6/2008 |
| EP | 1955989 A1 | 8/2008 |
| EP | 2248582 A2 | 2/2009 |
| JP | 1990000121 | 1/1990 |
| JP | 10-182532 A | 7/1998 |
| JP | 11293263 A | 10/1999 |
| JP | 2000169411 A | 6/2000 |
| JP | 2004161672 A | 6/2004 |
| JP | 2004161673 A | 6/2004 |
| JP | 2005104912 A | 4/2005 |
| WO | 0073404 A1 | 12/2000 |
| WO | 0198237 A1 | 12/2001 |
| WO | 2007023706 A1 | 3/2007 |
| WO | 2008055776 A1 | 5/2008 |
| WO | 2009132449 A1 | 11/2009 |
| WO | 2011089263 A1 | 7/2011 |

OTHER PUBLICATIONS

Japanese Patent No. 10182532; Date of Publication: Jul. 7, 1998; Machine Translation, 9 pages.
Japanese Patent No. 11293263; Date of Publication: Oct. 26, 1999; Abstract Only, 2 pages.
Japanese Patent No. 2000169411; Date of Publication: Jun. 20, 2000; Abstract Only, 2 pages.
Japanese Patent No. 2004161672; Date of Publication: Jun. 10, 2004; Abstract Only, 2 pages.
Japanese Patent No. 2004161673; Date of Publication: Jun. 10, 2004; Abstract Only, 2 pages.
Japanese Patent No. 2005104912; Date of Publication: Apr. 21, 2005; Abstract Only, 1 page.
A.V. Abramova et al., "Production of Lower Unsaturated Hydrocarbons via Catalytic Conversion of Dimethyl Ether". Petroleum Chemistry, 2008, vol. 48, No. 1, pp. 15-21; 7 pages.
Guangyu Cai et al., "Light alkenes from syngas via dimethyl ether". Applied Catalysis A: General 125 (1995); 10 pages.
B. Delmon et al., "Catalyst Deactivation 1999"; Book Review; React. Kinet.Catal.Lett vol. 70, No. 1, 191-193 (2000); 6 pages.
Mads Kaarsholm et al., "Phosphorous modified ZSM-5: Deactivation and product distribution for MTO". Chemical Engineering Science 62 (2007) 5527-5532; 6 pages.
S.N. Khadzhiev et al., "Manufacturing of Lower Olefins from Natural Gas through Methanol and Its Derivatives (Review)". Petroleum Chemistry, 2008, vol. 48, No. 5, pp. 325-334; 10 pages.
Yun Ha Kim et al., "Selective CO removal in the H2-rich stream through a double-bed system composed of non-noble metal catalysts"; Natural Gas Conversion VIII; 2007, 6 pages.
O.V. Krylov et al., "The regularities in the interaction of alkanes with CO2 on oxide catalysts". Catalysis Today 24 (1995) 371-375; 5 pages.
Howon Lee et al., "Effect of Divalent Metal Component (ME II) on the Catalytic Performance of MEIIFE2O4 Catalysts in the Oxidative Dehydrogenation of n-Butene to 1,3-Butadiene". Catal Lett (2008) 124:365-368; 5 pages.
Yotaro Ohno et al., "Slurry Phase DME Direct Synthesis Technology—100 tons/day Demonstration Plant Operation and Scale Up Study", Natural Gas Conversion VIII; 2007, 6 pages.
Magnus Ronning et al., "Relating catalyst structure and composition to the water-gas shift activity of Cu—Zn-based mixed-oxide catalysts". Catalysis Today 100 (2005) 249-254; 6 pages.
Tian-Sheng Zhao et al., "Direct synthesis of propylene and light olefins from dimethyl ether catalyzed by modified H-ZSM-5". Catalysis Communications 7 (2006) 647-650; 4 pages.
International Patent Publication No. 0073404; Date of Publication: Dec. 7, 2000; Abstract Only, 2 pages.
International Patent Publication No. 0198237; Date of Publication: Dec. 27, 2001; Abstract Only, 2 pages.
International Patent Publication No. 2007023706; Date of Publication: Mar. 1, 2007; Abstract Only, 2 pages.
International Preliminary Report on Patentability and Written Opinion of the International Seaching Authority for PCT/EP2011/005375, May 7, 2013, 9 pages.
International Search Report for PCT/EP2011/005375, mailed Mar. 2, 2012, 5 pages.

* cited by examiner

PROCESS FOR PRODUCING LIGHT OLEFINS BY USING A ZSM-5-BASED CATALYST

CROSS REFERENCE TO RELATED APPLICATIONS

This application is a 371 of International Application No. PCT/EP2011/005375, filed Oct. 25, 2011, which claims priority to European Application No. 10014193.6, filed Nov. 2, 2010, both of which are incorporated herein by reference in their entirety.

TECHNICAL FIELD

The present invention relates to a catalyst composition useful in a process for producing lower olefins from a oxygenate feedstream, a process for producing said catalyst composition and a process for producing lower olefins comprising contacting an oxygenate feedstream with the catalyst composition of the present invention. In addition thereto, the present invention relates to an integrated process for producing lower olefins from a feedstream comprising hydrocarbons.

BACKGROUND ART

It is known from e.g. U.S. Pat. No. 4,025,575 that light oxygenates can be converted to the lower olefins ethylene and propylene using H-ZSM-5 zeolite as a catalyst.

U.S. Pat. No. 3,911,041 describes that methanol and DME can be converted to a reaction product containing olefins using a zeolite catalyst containing at least 0.78 wt-% phosphorus incorporated with the crystal structure of the zeolite. The zeolite used in the process of U.S. Pat. No. 3,911,041 may be ZSM-5. U.S. Pat. No. 3,911,041 further teaches that the activity of the phosphorus-containing zeolite catalyst can be increased by depositing zinc (Zn) on the zeolite.

U.S. Pat. No. 5,367,100 describes a method for the conversion of methanol or dimethyl ether to light olefins using a zeolite ZSM-5 based catalyst containing at least 0.7 wt-% phosphorus and at least 0.97 wt-% rare earth elements which are incorporated within the structure of the catalyst. The rare earth elements are preferably rich in lanthanum so that the content of lanthanum in the catalyst preferably is between 2.5 and 3.5 wt-%.

U.S. Pat. No. 4,049,573 describes a number of different boron or magnesium-comprising catalyst compositions useful for converting monohydric alcohols and their ethers to a hydrocarbon mixture ring in C2-C3 olefins and mononuclear aromatics.

The oxygenate-to-olefin catalysts of the prior art have the disadvantage that they have a relatively low selectivity for C2-C3 olefins and/or become quickly deactivated by coke deposition on the catalyst surface.

DISCLOSURE OF INVENTION

It was an object of the present invention to provide an improved process for converting oxygenates to olefins.

Accordingly, the present invention provides a process for producing lower olefin, preferably ethylene and propylene, comprising an olefin synthesis step wherein the lower olefin is produced by contacting the catalyst composition comprising $M_1$-$M_2$-P/ZSM-5 with an oxygenate-comprising feedstream, wherein $M_1$ is one or more basic species, $M_2$ is one or more redox elements selected from Groups 6-8 of the Periodic Table of Elements and Sn and P is phosphorus, wherein said basic species is a molecular entity forming a weak Lewis base and/or a weak Brnsted base in the catalyst composition.

In the context of the present invention, it was surprisingly found that a catalyst composition comprising ZSM-5 zeolite which is modifying with one or more basic species (e.g. Mg, Ca, Sr, La and Zr or amphoteric oxide or hydroxide of Mn); one or more redox elements (e.g. Fe, Mn Cr, W and Sn or Mn not forming an amphoteric oxide or hydroxide); and phosphorus is a particularly advantageous for converting oxygenates to lower olefins. For instance, the total selectivity to C2-C3 olefins in an oxygenate-to-olefins process could be significantly increased by using the catalyst composition comprising $M_1$-$M_2$-P/ZSM-5 as described herein. The catalyst of the present invention is more resistant to coke formation and shows a more stable catalyst performance than conventional oxygenate-to-olefin catalysts based on silicoaluminophosphate molecular sieves.

Without being bound by theory, it is believed that strong acidic properties leads to the formation of high molecular hydrocarbons through involvement of more $H^+$ surface fragments or more strong $H^+$ sites of O—$H^+$ surface centres keeping strongly the reaction intermediates on the surface with their consecutive oligomerization. Accordingly, it is believed that a ZSM-5 catalyst for producing lower olefins from an oxygenate feed having a low selectivity to LPG and high molecular weight hydrocarbons and which is resistant to coke formation is obtained when the acid properties of the catalyst are reduced. Replacement of surface $H^+$ protons with other basic property elements would allow eliminating $H^+$ protons to form metal-zeolite framework and to decrease the acidic properties of the zeolite.

The term "weak basic species" as used herein relates to an molecular entity that forms a weak "Lewis base" (i.e. an element that is able to provide a pair of electrons and thus capable of coordination to a Lewis acid, thereby producing a Lewis adduct) and/or a weak "Brnsted base" (i.e. an element capable of accepting a proton from a acid or the corresponding chemical species) in the catalyst composition. The term "weak base" is amply known in the art and relates to a base that does not ionize fully in an aqueous solution.

Preferably, the basic species is selected from the group consisting of alkaline earth metals, rare earth elements and elements forming amphoteric oxide or hydroxide. The alkaline earth metals (or Group 2 elements of the Periodic Table of Elements) that preferably may be comprised in the catalyst composition are selected from the group consisting of Be, Mg, Ca, Sr, and Ba and more preferably selected from the group consisting of Mg, Ca and Sr. The preferred rare earth element (i.e. the group of elements consisting of the lanthanides, Sc and Yt) that may be comprised in the catalyst composition is La. In the context of the present invention, the term "basic species" also includes amphoteric species, i.e. a molecule or ion that can react as a base (besides being able to react as an acid under different conditions). Amphoteric species are well known in the art and include oxides or hydroxides of metals. A preferred amphoteric species that may be comprised as basic species in the catalyst composition used in the present process is an amphoteric oxide or hydroxide of Mn, most preferably MnO.

Accordingly, particularly preferred basic species in the context of the present invention is an element selected from the group consisting of Mg, Ca, Sr, La and Zr; or an amphoteric oxide or hydroxide of Mn.

The catalyst composition of the present invention preferably comprises at least 0.5 wt-%, more preferably at least 1 wt-% and most preferably at least 2 wt-% basic species and preferably comprises up to 12 wt-%, more preferably up to 10 wt-% and most preferably up to 8 wt-% basic element.

The term "redox element" as used herein relates to an element that forms different oxides with at least two different valencies and which can easily change from one valence to another one. Preferred redox elements in the context of the present invention are selected from the group consisting of Fe, Cr, W and Sn or Mn not forming an amphoteric oxide or hydroxide thereof (non-amphoteric Mn) and more preferably are selected from the group consisting of Fe and Cr or non-amphoteric Mn. The catalyst composition of the present invention preferably comprises at least 0.5 wt-% redox element, more at least 1 wt-% redox element, even more preferably at least 2 wt-% redox element and most preferably at least 3 wt-% redox element and preferably comprises up to 12 wt-% redox element, more preferably up to 11 wt-% redox element and most preferably up to 10 wt-% redox element. Without being bound by theory, it is believed that the presence of redox element leads to a decrease of coke formation.

The catalyst composition used in the process of the present invention preferably comprises at least 0.5 wt-% phosphorus, more at least 1 wt-% phosphorus, even more preferably at least 2 wt-% phosphorus and most preferably at least 3 wt-% phosphorus and preferably comprises up to 12 wt-% phosphorus, more preferably up to 11 wt-% phosphorus and most preferably up to 10 wt-% phosphorus. Without being bound by theory, it is believed that the phosphorus regulates the acidic property of the zeolite, which allows obtaining high conversion and reduced catalyst coking.

The microporous aluminosilicate zeolite "ZSM-5", which is also known as "MFI" zeolite, is well known in the art and can be commercially obtained or synthesized; see e.g. Singh and Dutta (2003) in Handbook of zeolite science and technology, eds. Auerbach et al. pp 21-64.

The skilled person is readily capable of selecting a ZSM-5 zeolite having a suitable Si/Al ratio. When the Si/Al ratio is too high, the catalyst activity is reduced. At a too low Si/Al ratio catalyst coking is increased. Preferably, the Si/Al ratio of the ZSM-5 zeolite is at least 20, more preferably at least 30 and preferably up to 150 more preferably up to 80. Most preferably, the Si/Al ratio of the ZSM-5 zeolite is about 40.

The catalyst composition used in the process of the present invention may further comprise a binder. Silica ($SiO_2$) is the preferred binder since it has chemically neutral properties when used as a catalyst in an oxygenate-to-olefin process. Binders having high acidic properties such as alumina ($Al_2O_3$) are less preferred since they may induce aromatization, which is not desired in an oxygenate-to-olefin process. The catalyst composition of the present invention preferably comprises at least 10 wt-%, most preferably at least 20 wt-% binder and preferably comprises up to 40 wt-% binder.

Most preferably, the catalyst composition comprises the basic element Ca, the redox element Mn and $SiO_2$ binder. In a further most preferred embodiment of the present invention, the catalyst composition comprises the basic element Mg and the redox element Cr without binder.

In a further aspect, the catalyst composition used in the process of the present invention is prepared by the method comprising the steps of:
(i) contacting ZSM-5 zeolite with one or more solutions comprising soluble salts of $M_1$, soluble salts of $M_2$ and phosphoric acid to modify said ZSM-5 with $M_1$, $M_2$ and P; and
(ii) drying and calcining the modified ZSM-5 zeolite in an oxygen-comprising atmosphere.

Accordingly, the ZSM-5 zeolite is contacted with a solution in which one or more basic elements $M_1$; one or more redox elements $M_2$; and the phosphoric acid are dissolved. Preferably, the solution is an aqueous solution. Preferred soluble salts of $M_1$ and $M_2$ are nitrate salts. Preferred soluble salts of the basic element $M_1$ are selected from the list consisting of $Mg(NO_3)_2$, $Ca(NO_3)_2$, $Sr(NO_3)_2$, $La(NO_3)_3$ and $Zr(NO_3)_4$. Preferred soluble salts of the redox element $M_2$ are selected from the list consisting of $Fe(NO_3)_2$, $Mn(NO_3)_2$ $Cr(NO_3)_2$, $H_3WO_4$ and $Sn(NO_3)_2$.

The phosphorus (P) may be deposited by contacting the ZSM-5 zeolite with phosphoric acid ($H_3PO_4$) solution (e.g. 89 wt-% $H_3PO_4$ in water).

The basic element(s) $M_1$, redox element(s) $M_2$ and phosphorus (P) may be deposited by contacting the ZSM-5 zeolite with a single solution in which the soluble salts of $M_1$, soluble salts of $M_2$ and phosphoric acid are dissolved. Alternatively, the basic element(s) $M_1$, redox element(s) $M_2$ and phosphorus (P) may be deposited by subsequently contacting the ZSM-5 zeolite with the different elements and/or phosphorus, whereby the composition is dried to evaporate the solvent before contacting the composition with the following element. After depositing the all required elements, the obtained composition (catalyst precursor) is dried. In one embodiment of the present invention, the catalyst precursor is dried in air, preferably for about 8 hours at about 60-80° C. while stirring.

After drying, the ZSM-5-comprising composition on which the basic element $M_1$, the redox element $M_2$ and the phosphorus (P) are deposited is calcined in an oxygen-comprising atmosphere, preferably in moisture-free atmospheric air. Preferably, the catalyst precursor is calcined at about 450-550° C. and a pressure of about 0.1 MPa. for 4-6 hrs. Most preferably the catalyst precursor is calcined at about 500° C. for about 4 hrs.

When a binder is present, it is preferred that the ZSM-5 zeolite is mixed with the binder prior to contacting the ZSM-5 zeolite with one or more solutions comprising soluble salts of $M_1$, soluble salts of $M_2$ and phosphoric acid.

Accordingly, a process for producing a lower olefin is provided comprising an olefin synthesis step wherein said lower olefin is produced by contacting the catalyst composition of the present invention with a feedstream comprising an oxygenate. Preferably, the oxygenate is selected from the group consisting of dimethyl ether (DME), diethyl ether, methanol (MeOH) and ethanol (EtOH) or a mixture thereof. Also a mixture of e.g. DME and MeOH may be used as oxygenate feedstream. Preferably, the "lower olefin" produced in the "oxygenate-to-olefins process" of the present invention is a mixture of ethylene ($C_2H_4$) and propylene ($C_3H_6$).

Accordingly, the present invention provides a process for producing a lower olefin comprising the steps of:
(i) contacting ZSM-5 zeolite with one or more solutions comprising soluble salts of $M_1$, soluble salts of $M_2$ and phosphoric acid to modify said ZSM-5 with $M_1$, $M_2$ and P;
(ii) drying and calcining the modified ZSM-5 zeolite in an oxygen-comprising atmosphere to provide the catalyst comprising $M_1$-$M_2$-P/ZSM-5 as defined herein; and
(iii) contacting said catalyst comprising $M_1$-$M_2$-P/ZSM-5 with a feedstream comprising an oxygenate.

The process conditions useful in a process for converting oxygenate-to-olefins can be easily determined by the person skilled in the art; see e.g. Rayford G. Anthony (1978) Catalytic conversion of oxygenated Compounds to low molecular weight olefins. Accordingly, the temperature may be about 350-500° C. and preferably about 500° C. Furthermore, the oxygenate-to-olefins process as described herein preferably is performed at a WHSV of approximately 2.0 h$^{-1}$ and/or at atmospheric pressure.

It is an advantage of the present invention that the catalyst is more resistant to coke-deposition. Would the oxygenate-to-olefins catalyst "$M_1$-$M_2$-P/ZSM-5" of the present invention nevertheless become deactivated e.g. by coke deposition it can be regenerated using conventional methods. In one embodiment, the oxygenate-to-olefins catalyst (i.e. the catalyst used in the oxygenate-to-olefins process of the present invention or the "olefin synthesis step" as defined herein) is regenerated by contacting the catalyst at a temperature of about 550-600° C. with an oxygen-comprising gas stream, such as an atmospheric air stream.

In a further embodiment, the oxygenate-comprising feedstream used in the oxygenate-to-olefins process of the present invention is produced by a process comprising:

(i) a syngas producing step, wherein a syngas composition is produced by contacting a syngas producing catalyst with a hydrocarbon feedstream comprising hydrocarbons (HC), oxygen ($O_2$) and carbon-dioxide ($CO_2$); and (ii) an oxygenate synthesis step, wherein dimethyl ether (DME), methanol (MeOH) or a mixture thereof is produced by contacting an oxygenate synthesis catalyst with the syngas composition of step (i).

As used herein, the term "hydrocarbon feedstream" relates to the hydrocarbon-comprising stream which is fed to the syngas producing step and which further comprises $O_2$ and $CO_2$. Preferably, the "hydrocarbon feedstream" is gaseous when contacted with the syngas producing catalyst. Preferably, the hydrocarbons comprised in the hydrocarbon feedstream are C1-C15 hydrocarbons (i.e. hydrocarbons comprising 1-15 carbon atoms). A further characterizing aspect of the hydrocarbons-to-olefins process as described herein accordingly is that the syngas producing step represents a combination of different processes including partial oxidation, oxidative cracking and dry reforming. Optionally, by-products produced in the syngas producing step, such as olefins, may be separated and removed from the produced syngas composition before said syngas composition is fed to the oxygenate synthesis step. As used herein, the term "dry reforming" means $CO_2$ conversion to CO. Oxidative dry cracking has the advantage that oxygen presence gives exothermic reaction and heat production, and that dry reforming addition of $CO_2$ allows to involve $CO_2$ to the reaction and produce CO from $CO_2$ as well.

$CO_2$ comprised in the product stream produced in the syngas producing step, oxygenate synthesis step and/or olefin synthesis step may be recycled back e.g. to the hydrocarbon feedstream which is fed to the syngas producing step. CO and/or $H_2$ comprised in the product stream produced in the olefin synthesis step may be recycled to the syngas composition which is fed to the oxygenate synthesis step.

Accordingly, in one embodiment the present invention relates to an integrated process for producing lower olefin from hydrocarbons wherein the $CO_2$ comprised in the syngas composition produced in the herein defined "syngas producing step" and the $CO_2$ comprised in the oxygenate stream produced in the herein defined "oxygenate synthesis step" is separated and recycled to the hydrocarbon feedstream; the carbon-monoxide (CO) and hydrogen ($H_2$) comprised in the product stream produced in the "oxygenate-to-olefin process" of the present invention are separated and recycled to the oxygenate synthesis feedstream; and the reaction products other than the lower olefins, carbon-monoxide (CO) and hydrogen ($H_2$) comprised in the product stream produced in the "oxygenate-to-olefin process" of the present invention are separated and are recycled to the hydrocarbon feedstream of the "syngas producing step". Preferably, the unreacted syngas comprised in the product produced in the oxygenate synthesis step is separated and recycled to the oxygenate synthesis feedstream.

Accordingly, substantially all carbon-comprising by-products produced in the integrated process of the present invention (e.g. CO, $CO_2$, $CH_4C_2H_6$, $C_3H_8$ and C4$^+$ hydrocarbons) are recycled back to the integrated hydrocarbon-to-olefins process of the present invention. Hence, one advantage of the integrated process of the present invention is realization of high carbon efficiency without using additional downstream processes.

The total selectivity to ethylene and propylene in the oxygenate-to-olefins process of the present invention is about 72-75 mole-%. Accordingly, the product stream of the olefin-synthesis step only comprises about 25-28 mole-% of by-products (products comprised in the product stream produced in the olefin synthesis step other than lower olefins such as ethylene and propylene). These by-products include, but are not limited to, hydrocarbons other than lower olefins, $CO_2$, CO and $H_2$. The volume of the by-products is about 20-35% vol-% of the "hydrocarbon feedstream" as defined herein above and which is fed to syngas producing step.

In one embodiment the syngas producing catalyst is a Ni-comprising supported catalyst, preferably selected from the group consisting of Ni—/$Al_2O_3$-comprising catalyst; Ni—/$La_2O_2$-comprising catalyst; Ni—/$CeO_2$-comprising catalyst; Ni—/$ZrO_2$-comprising catalyst; or a catalyst selected from the group consisting of La—Ni—/$Al_2O_3$-comprising catalyst; Ce—Ni—/$Al_2O_3$-comprising catalyst; La—/$Al_2O_3$-comprising catalyst; Ni—Ce—$ZrO_2$-comprising catalyst; Ni—$ZrO_2$—$CeO_2$—$TiO_2$-comprising catalyst; and Rh—$CeO_2$/$ZrO_2$-comprising catalyst; see also US 2006/0216227, WO 2008/055776, and US 2008/0260628

The process conditions useful in the syngas producing step can be easily determined by the person skilled in the art; see e.g. "Hydrogen and Syngas Production and Purification Technologies" (2010) eds. Ke Lu et al. Accordingly, the temperature may be about 500-1200° C. and preferably about 850-900° C. Furthermore, the syngas producing step as described herein preferably is performed at a pressure about 0.2-2.5 MPa.

In one embodiment the oxygenate synthesis catalyst is a Cu-comprising supported catalyst, preferably selected from the group consisting of Cu—/ZnO-comprising catalyst; Cu—/ZnO/$Al_2O_3$-comprising catalyst; CuO/ZnO/$Al_2O_3$-comprising catalyst; Cu—/ZnO/$Cr_2O_3$-comprising catalyst; Cu—/$ZrO_2$-comprising catalyst; CuO/ZnO/$Al_2O_3$-comprising catalyst; and CuO/ZnO/$Al_2O_3$/$SiO_2$-comprising catalyst; see also WO 2009/132449.

The process conditions useful in oxygenate producing step can be easily determined by the person skilled in the art; see e.g. WO 2009/132449. Accordingly, the temperature may be about 220-320° C. and preferably about 220-250° C. Furthermore, the oxygenate producing step as described herein preferably is performed at a pressure of about 0.5-6.5 MPa, preferably at about 6 MPa.

FIGURES

FIG. 1 illustrates the integrated process for producing lower olefins from hydrocarbons (HC) using the catalyst and the process of the present invention. This integrated process has the advantage that lower olefins can be produced with up to 100% carbon efficiency. In this embodiment, the unreacted syngas is not separated from the oxygenate product produced in the oxygenate synthesis step.

Figure 2:
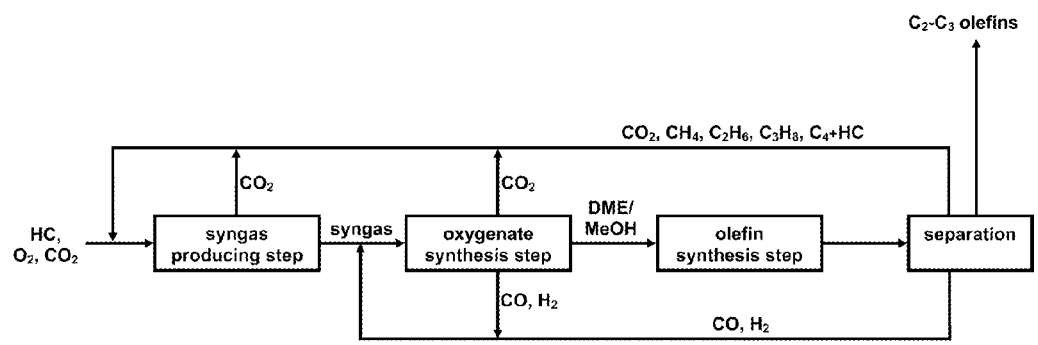

FIG. 2 illustrates the integrated process for producing lower olefins from hydrocarbons (HC) using the catalyst and the process of the present invention. This integrated process has the advantage that lower olefins can be produced with up to 100% carbon efficiency. In this embodiment, the unreacted syngas is separated from the oxygenate product produced in the oxygenate synthesis step. This has the additional advantage that the catalyst performance in the olefin synthesis step is more stable.

MODE(S) FOR CARRYING OUT THE INVENTION

The present invention will now be more fully described by the following non-limiting Examples.

Example 1

Si—Ca—La—Sr—Cr—P/ZSM-5 Catalyst Composition

The 2.28 wt % Si-5 wt % Ca-5 wt % La-5 wt % Sr-5 wt % Cr-5 wt % P/ZSM-5 catalyst has been prepared as follows. The suitable amount of zeolite ZSM-5 (MFI) was mixed with $SiO_2$ gel (40 wt-% $SiO_2$ gel in water). Subsequently, aqueous solutions of $Ca(NO_3)_2$ and $La(NO_3)_3$ and $H_3PO_4$ (89 wt-% in water) were added to the mixture in amounts leading to 5 wt-% Ca, 5 wt-% La and 5 wt-% P in the ready catalyst. The mixture was then kept for 8 hours at 60° C. while stirring to evaporate the water. The obtained solid material was further dried overnight at 120° C. The dried solid material was subsequently impregnated with solutions of $Cr(NO_3)_3$ and $Sr(NO_3)_2$ in water leading to 5 wt-% Cr and 5 wt-% Sr in the ready catalyst. The impregnated catalyst precursor mixture was then kept for 8 hours at 60° C. while stirring to evaporate the water. The impregnated solid material was further dried overnight at 120° C. and calcined for 4 hours at 400° C. in atmospheric air to obtain the 2.28 wt % Si-5 wt % Ca-5 wt % La-5 wt % Sr-5 wt % Cr-5 wt % P/ZSM-5 catalyst composition.

The prepared 2.28 wt % Si-5 wt % Ca-5 wt % La-5 wt % Sr-5 wt % Cr-5 wt % P/ZSM-5 catalyst composition was subsequently used to convert DME to olefins. Therefore, 0.2 ml of solid catalyst material was loaded to the fixed bed reactor, treated for 1 hour at 470° C. with air before switching to an oxygenate-comprising feedstream consisting of 44 mole-% DME and 56 mole-% $N_2$ at a total flow of 62 cc/min and a temperature of 470° C.

The hydrocarbon distribution in the outlet gas as measured on the basis of gas-chromatography analysis is summarized in the herein below provided Table 1. The calculations are based on carbon numbers at full conversion of the DME.

Example 2

Fe—Mn—P/ZSM-5 Catalyst Composition

A 3 wt % Fe-8 wt % Mn-10 wt % P/ZSM-5 catalyst composition was prepared using the same method as described in Example 1. Shortly, a suitable amount of ZSM-5 zeolite was mixed with aqueous solutions of $Fe(NO_3)_3$ and $Mn(NO_3)_2$ and $H_3PO_4$ (89% in water) leading to 8 wt-% Mn and 10 wt-% P in the ready catalyst. The mixture was then kept for 8 hours at 60° C. while stirring to evaporate the water. The obtained solid material was further dried overnight at 120° C. The dried solid material was calcined for 4 hours at 400° C. in atmospheric air. As a result thereof, the comprised Mn forms a basic species in the catalyst composition.

The prepared 3 wt % Fe-8 wt % Mn-10 wt % P/ZSM-5 catalyst composition was subsequently used to convert DME to olefins. Therefore, 0.2 ml of solid catalyst composition material was loaded to the reactor, treated for 1 hour at 470° C. with air before switching to an oxygenate-comprising feedstream consisting of 44 mole-% DME and 56 mole-% $N_2$ at a total flow of 62 cc/min and a temperature of 470° C.

The hydrocarbon distribution in the outlet gas is summarized in the herein below provided Table 1.

Example 3

Comparative

ZSM-5 Catalyst Composition

In this example the experiment on DME conversion has been realized as in example 1 but in the presence of non-modified ZSM-5 catalyst. It is necessary to note that in the presence of non-modified zeolite ethylene selectivity is very low and the predominant lower olefin comprised in the outlet gas stream is propylene.

Example 4

Comparative

Mg—P/ZSM-5 Catalyst Composition

The Mg—P/ZSM-5 catalyst composition was prepared as in Example 1 with the exception that MgO powder was used to prepare the catalyst instead of La, Sr, Mn salts. Accordingly, a suitable amount of MgO powder was dissolved in an aqueous $H_3PO_4$ solution which was added 10 g of ZSM-5 zeolite. Subsequently, a catalyst having the composition 4 wt % Mg-6 wt % P/ZSM-5 was obtained.

The prepared 4 wt % Mg-6 wt % P/ZSM-5 catalyst composition was subsequently used to convert DME to olefins. Therefore, 0.2 ml of solid catalyst composition material was loaded to the reactor, treated for 1 hour at 470° C. with air before switching to an oxygenate-comprising feedstream consisting of 44 mole-% DME and 56 mole-% $N_2$ at a total flow of 62 cc/min and a temperature of 470° C.

The hydrocarbon distribution in the outlet gas is summarized in the herein below provided Table 1.

Example 5

Comparative

Zr—P/ZSM-5 Catalyst Composition 10 g of ZSM-5 was mixed with 200 ml water. The correct amounts of $ZrCl_4$ and $H_3PO_4$ were added to the mixture to obtain 12 wt-% Zr and 5 wt-% P in the ready catalyst. The suspension was stirred for 8 hours at 60° C. When water was evaporated the dry material was kept overnight at 120° C. and subsequently was calcined for 4 hours at 400° C.

The prepared 12 wt % Zr-5 wt % P/ZSM-5 catalyst composition was subsequently used to convert DME to olefins. Therefore, 0.5 ml of solid catalyst composition material was loaded to the reactor, treated for 1 hour at 470° C. with air before switching to an oxygenate-comprising feedstream consisting of 44 mole-% DME and 56 mole-% $N_2$ at a total flow of 62 cc/min and a temperature of 470° C.

The hydrocarbon distribution in the outlet gas is summarized in the herein below provided Table 1.

TABLE 1

Hydrocarbon-composition of outlet gas (mole-%)

|  | Example 1 | Example 2 | Example 3 (comp.) | Example 4 (comp.) | Example 5 (comp.) |
|---|---|---|---|---|---|
| Methane | 4.11 | 7.98 | 7.20 | 1.03 | 12.64 |
| Ethane | 0.39 | 0.68 | 0.56 | 0.38 | 0.60 |
| Ethylene | 29.17 | 24.25 | 5.25 | 27.51 | 25.77 |
| Propane | 1.83 | 1.98 | 4.30 | 3.91 | 0.92 |
| Propylene | 50.05 | 51.30 | 60.29 | 47.27 | 46.33 |
| C4+ | 14.54 | 13.815 | 22.40 | 19.83 | 12.74 |
| C2-C3 olefins selectivity | 75.3 | 75.5 | 64.12 | 68.8 | 73.8 |

As shown in Table 1 it was found that the total selectivity to C2-C3 olefins could be increased to at least 75 mole-% by using the process of the present invention. Moreover, it was found that catalyst performance is stable for about 10 hours. Conventional oxygenate-to-olefin catalysts based on silicoaluminophosphate molecular sieves such as SAPO-34 are known to deactivate within 2 hrs, which necessitates the use of a circulating fluidized bed reactor; see e.g. Cai et al. (1995) Applied Catal 125: 29-38. In the present Examples the catalyst was regenerated by contacting the catalyst with an air flow of 50 cc/min at 470° C.

Example 6

Diethyl Ether Conversion Using Si—Ca—La—Sr—Cr—P/ZSM-5 Catalyst

Example 6 is identical to Example 1 with the exception that the oxygenate diethyl ether has been used in the feed instead of dimethyl ether (DME). Diethyl ether conversion was 100 mole-%.

TABLE 2

Hydrocarbon composition of outlet gas (mole-%)

|  | Example 6 |
|---|---|
| Methane | 3.0 |
| Ethane | 4.2 |
| Ethylene | 78.5 |
| Propane | 2.1 |
| Propylene | 5.1 |
| C4+ | 7.1 |
| C2-C3 olefins selectivity | 80.5 |

Examples 7-11

Preparation of Syngas Using Ni-Lanthana Catalyst

Example 7

Preparation of Ni-Lanthana Catalyst

The 3 wt % $Ni/La_2O_3$ oxidative cracking catalyst for the oxidative cracking of methane was prepared as follows: 2 ml $La_2O_3$ particles of 25-40 mesh size were loaded in the quartz reactor with an inner diameter of 12 mm and a length of 45 cm. The loaded reactor was fed with a gaseous mixture consisting of approximately 28.4% mole $CH_4$+11% mole $O_2$+17.4% mole $CO_2$+42.8% mole $N_2$ at 450° C. After treatment of the support with reaction mixture (less than 24 hours) to obtain a stable phase composition, impregnation of the $La_2O_3$ support with a 0.1-0.3% $Ni(NO_3)_2$ solution in water was started. Therefore the 0.1-0.3% $Ni(NO_3)_2$ solution was fed to the $La_2O_3$ support by injecting into the gas stream to gradually impregnate the $La_2O_3$ support with the Ni salt. The $Ni(NO_3)_2$ impregnation of the $La_2O_3$ support was continued until the calculated amount of 3 mass % $Ni/La_2O_3$ basis was reached. Formation of $NO_2$ was observed during the $Ni(NO_3)_2$ impregnation step which indicates that oxides of Ni are formed within the $La_2O_3$ support.

After completing the $Ni(NO_3)_2$ impregnation step, the reaction temperature was increased to 660° C. to reduce the Ni-oxide with the methane containing gaseous mixture (as above). The resultant in situ prepared cracking catalyst initially fully oxidizes methane to $CO_2$. However after reaching steady state condition the 3% $Ni/La_2O_3$ catalyst forms CO and $H_2$.

Example 8

Methane Conversion Using Ni-Lanthana Catalyst

Syngas is produced by contacting a feedstream consisting of 28.4 $CH_4$, 17.4 mole-% $CO_2$, 42.8 mole-% $N_2$ and 11.0 mole-% $O_2$ with the above described 3 wt % $Ni/La_2O_3$ catalyst at 750° C. Flow rate of the feed was 60 cc/min over a 0.5 ml catalyst bed. The outlet reaction mixture composition consisted of 28.6 mole-% CO, 36.9 mole-% $H_2$, 1.94 mole-% $CH_4$, 2.55 mole-% $CO_2$, 0.37 mole-% $O_2$ and 29.5 mole-% $N_2$. $CH_4$ conversion was 90.1 mole-% and $CO_2$ conversion was 78.7 mole-%.

Example 9

Ethane Conversion Using Ni-Lanthana Catalyst

Example 9 is identical with Example 8 with the exception that a feedstream comprising ethane has been used. Accordingly, the feedstream of Example 9 consisted of 21.8 mole-% $CO_2$, 39.4 mole-% $N_2$, 24 mole-% $CH_4$, 10.2 mole-% $O_2$ and 4.4 mole-% $C_2H_6$. The outlet composition of Example 9 consisted of 27.4 mole-% CO, 3.61 mole-% $CO_2$, 31.5 mole-% $N_2$, 2.01 mole-% $CH_4$, 34.9 mole-% $H_2$, 0.42 mole-% $O_2$ and 0.0005 mole-% $C_2H_6$. $CH_4$ conversion was 89.5 mole-%, $CO_2$ conversion was 79.3 mole-% and $C_2H_6$ conversion was 100 mole-%.

Example 10

Isobutane Conversion Using Ni-Lanthana Catalyst

Example 10 is identical with Example 8 with the exception that a feedstream comprising isobutane and isobutylene has been used. Accordingly, the feedstream of Example 10 consisted of 21.4 mole-% $CO_2$, 39.0 mole-% $N_2$, 24.4 mole-% $CH_4$, 10.0 mole-% $O_2$, 2 mole-% $iC_4H_8$ and 3 mole-% $i-C_4H_{10}$. The outlet composition of Example 10 consisted of 32.1 mole-% CO, 3.06 mole-% $CO_2$, 27.5 mole-% $N_2$, 3.28 mole-% $CH_4$, 33.5 mole-% $H_2$, 0.4 mole-% $O_2$, 0.009 mole-% $iC_4H_8$ and 0.012 mole-% $iC_4H_{10}$. $CH_4$ conversion was 81.0 mole-%, $CO_2$ conversion was 79.7 mole-%, $iC_4H_8$ conversion was 100 mole-% and $i-C_4H_{10}$ conversion was 100 mole-%.

Example 11

Light Naphtha Conversion Using Ni-Lanthana Catalyst

In this example as a hydrocarbon feed for generation of syngas has been used light naphtha using catalyst described in example 7. The temperature of the reaction was 800° C., $CO_2$+ air flow rate was 43 cc/min, flow rate of liquid light naphtha was 0.1 cc/min. The outlet composition of Example 11 consisted of 22 mole-% $H_2$, 6 mole-% CO, 7 mole-% $N_2$, 11.9 mole-% $C_2H_4$, 4.19 mole-% $C_2H_6$, 28.6 mole-% $CH_4$, 7.08 mole-% $CO_2$, 0.38 mole-% $C_3H_6$, 0.48 mole-% $C_4$, 8.18 mole-% benzene and 5.05 mole-% xylene. The light naphtha conversion was 100 mole-%.

Experiments showed that catalyst performance was stable for more than 5 hours. After 5 hours screening of catalyst feeding only the air without naphtha through the catalyst did show formation of $CO_2$. This experiment showed that within 5 hours there was not formation of coke fragments in Naphtha+$CO_2$+$O_2$ mixture which could be oxidized to $CO_2$ during treatment with air.

The invention claimed is:

1. A process for producing lower olefins comprising:
   contacting a catalyst composition with an oxygenate-comprising feedstream to produce the lower olefin, wherein the catalyst composition comprises
   $M_1$, $M_2$, P, and ZSM-5 zeolite,
   wherein
   $M_1$ comprises one or more basic species selected from the group consisting of alkaline earth metals, rare earth elements, and elements forming amphoteric oxide or hydroxide;
   $M_2$ comprises at least 0.5 wt-% of one or more redox elements selected from the group consisting of Fe, Cr, W, and Sn or Mn not forming an amphoteric oxide or hydroxide; and
   P is phosphorus.

2. The process according to claim 1, wherein the basic species is an element selected from the group consisting of Mg, Ca, Sr, La and Zr; or an amphoteric oxide or hydroxide of Mn.

3. The process according to claim 1, wherein the catalyst further comprises a binder.

4. The process according to claim 1, wherein the basic species is Ca and the redox element is Mn not forming an amphoteric oxide or hydroxide; or wherein the basic element is Mg and the redox element is Cr.

5. The process according to claim 1, wherein the oxygenate is selected from the group consisting of dimethyl ether (DME), diethyl ether, methanol (MeOH), and ethanol (EtOH).

6. The process according to claim 1, further comprising:
   (i) a syngas producing step, wherein a syngas composition is produced by contacting a syngas producing catalyst with a hydrocarbon feedstream comprising hydrocarbons (HC), oxygen ($O_2$) and carbon-dioxide ($CO_2$); and
   (ii) an oxygenate synthesis step, wherein dimethyl ether (DME), methanol (MeOH) or a mixture thereof is produced by contacting an oxygenate synthesis catalyst with the syngas composition of step (i)
   to produce the oxygenate-comprising feedstream prior to contacting the catalyst composition with the oxygenate-comprising feedstream.

7. The process according to claim 6, wherein the process is an integrated process wherein:
   the $CO_2$ comprised in the syngas composition produced in step (i) and the $CO_2$ comprised in the oxygenate stream produced in step (ii) is separated and recycled to the hydrocarbon feedstream;
   the carbon-monoxide (CO) and hydrogen ($H_2$) comprised in the product stream produced in the olefin synthesis step are separated and recycled to the oxygenate synthesis feedstream; and
   the reaction products other than the lower olefins, carbon-monoxide (CO) and hydrogen ($H_2$) comprised in the product stream produced in the olefin synthesis step are separated and are recycled to the hydrocarbon feedstream.

8. The process according to claim 6, wherein the syngas producing catalyst is a Ni-comprising supported catalyst.

9. The process according to claim 6, wherein the oxygenate synthesis catalyst is a Cu-comprising supported catalyst.

10. The process according to claim 1, further comprising:
    contacting the ZSM-5 zeolite with one or more solutions comprising soluble salts of $M_1$, soluble salts of $M_2$ and phosphoric acid to modify said ZSM-5 zeolite with $M_1$, $M_2$, and P; and
    drying and calcining the modified ZSM-5 zeolite in an oxygen-comprising atmosphere to prepare the catalyst composition prior to contacting the catalyst composition with the oxygenate-comprising feedstream.

11. The process according to claim 10, wherein the ZSM-5 zeolite is mixed with a binder prior to contacting the ZSM-5 zeolite with one or more solutions comprising soluble salts of $M_1$, $M_2$, and phosphoric acid.

12. The process according to claim 3, wherein the binder comprises silica.

13. The process according to claim 1, wherein the basic species is selected from the group consisting of Ca, La, and Sr, and the redox element is Cr.

14. The process according to claim 1, wherein the basic species is selected from the group consisting of an amphoteric oxide or hydroxide of Mn, and the redox element is Fe.

15. The process according to claim 1, wherein the catalyst composition comprises:
    0.5 wt-% to 12 wt-% of the basic species,
    0.5 wt-% to 12 wt-% of the redox element, and
    0.5 wt-% to 12 wt-% of the phosphorus.

* * * * *